(12) United States Patent
Yi et al.

(10) Patent No.: US 11,325,004 B2
(45) Date of Patent: May 10, 2022

(54) METHOD FOR SETTING DIFFICULTY LEVEL OF TRAINING CONTENTS AND ELECTRONIC DEVICE IMPLEMENTING THE SAME

(71) Applicant: NEOFECT CO., LTD., Yongin-si (KR)

(72) Inventors: Hyo Seok Yi, Yongin-si (KR); Hyun Soo Kim, Seoul (KR); Ho Yeong Song, Yongin-si (KR)

(73) Assignee: NEOFECT CO., LTD., Gyeonggi-Do (KR)

( * ) Notice: Subject to any disclaimer, the term of this patent is extended or adjusted under 35 U.S.C. 154(b) by 557 days.

(21) Appl. No.: 16/327,460

(22) PCT Filed: Aug. 16, 2017

(86) PCT No.: PCT/KR2017/008866
§ 371 (c)(1),
(2) Date: Feb. 22, 2019

(87) PCT Pub. No.: WO2018/038449
PCT Pub. Date: Mar. 1, 2018

(65) Prior Publication Data
US 2019/0175989 A1    Jun. 13, 2019

(30) Foreign Application Priority Data
Aug. 24, 2016    (KR) .......................... 10-2016-0107987

(51) Int. Cl.
*G06F 3/048*    (2013.01)
*A63B 24/00*    (2006.01)
(Continued)

(52) U.S. Cl.
CPC ...... *A63B 24/0075* (2013.01); *A63B 71/0622* (2013.01); *G06Q 50/10* (2013.01);
(Continued)

(58) Field of Classification Search
CPC ...................... A63B 24/0075; A63B 71/0622; G06Q 50/10; G06Q 50/22
See application file for complete search history.

(56) References Cited

U.S. PATENT DOCUMENTS 7,480,512 B2 *    1/2009    Graham ................ H04W 4/029
                                                  455/456.3
9,526,443 B1 *    12/2016    Berme .................... G06F 3/147
(Continued)

FOREIGN PATENT DOCUMENTS

JP    2012157404 A    8/2012
KR    1020140082449 A    7/2014
(Continued)

OTHER PUBLICATIONS

International Search Report of PCT/KR2017/008866 dated Nov. 22, 2017, 4 pages.

*Primary Examiner* — David Phantana-angkool
(74) *Attorney, Agent, or Firm* — Hamre, Schumann, Mueller & Larson, P.C.

(57) ABSTRACT

The present disclosure relate to a method for setting a difficulty level of training contents and an electronic device implementing the same. A method for setting a difficulty level of training according to various embodiments of the present disclosure includes: checking a first reference value, which is a preset difficulty level for a first session, if the user wants to perform a training motion of the first session; providing the user with training contents corresponding to the checked first reference value during the first session; collecting the user's training details of the training performed during the first session; setting an increased difficulty level based on a second reference value, which is a preset difficulty level for a second session and the user's training details collected during the first session, if the user wants to perform a motion of the second session; and (Continued)

providing the user with training contents corresponding to the set increased difficulty level during the second session.

6 Claims, 7 Drawing Sheets

(51) Int. Cl.
    *G06Q 50/22*     (2018.01)
    *G06Q 50/10*     (2012.01)
    *A63B 71/06*     (2006.01)

(52) U.S. Cl.
    CPC ...... *G06Q 50/22* (2013.01); *A63B 2024/0068* (2013.01); *A63B 2024/0078* (2013.01); *A63B 2220/803* (2013.01)

(56) References Cited

U.S. PATENT DOCUMENTS

| | | | |
|---|---|---|---|
| 9,710,711 B2* | 7/2017 | Dibenedetto | A63F 13/211 |
| 10,082,396 B2* | 9/2018 | Ellis | G16H 20/40 |
| 10,234,936 B2* | 3/2019 | Tanaka | H04L 63/0861 |
| 10,918,908 B2* | 2/2021 | Toivonen | G16H 40/67 |
| 10,922,383 B2* | 2/2021 | Coza | G16H 40/63 |
| 2003/0224337 A1* | 12/2003 | Shum | G16H 20/30 434/247 |
| 2015/0268721 A1* | 9/2015 | Joo | G06F 3/013 345/156 |
| 2017/0010667 A1* | 1/2017 | Tanaka | G06F 3/016 |
| 2017/0143262 A1* | 5/2017 | Kurunmaki | A61B 5/0255 |
| 2018/0085630 A1* | 3/2018 | Capell | A63B 24/0062 |
| 2018/0140902 A1* | 5/2018 | Wiebe | A41D 1/002 |
| 2020/0001134 A1* | 1/2020 | Rauhala | G16H 20/60 |
| 2020/0222756 A1* | 7/2020 | Sano | A61B 5/4088 |

FOREIGN PATENT DOCUMENTS

| | | |
|---|---|---|
| KR | 101438006 B1 | 9/2014 |
| KR | 1020140115120 A | 9/2014 |
| KR | 101541099 B1 | 8/2015 |
| KR | 1020160046082 A | 4/2016 |
| WO | 2015179522 A1 | 11/2015 |

* cited by examiner

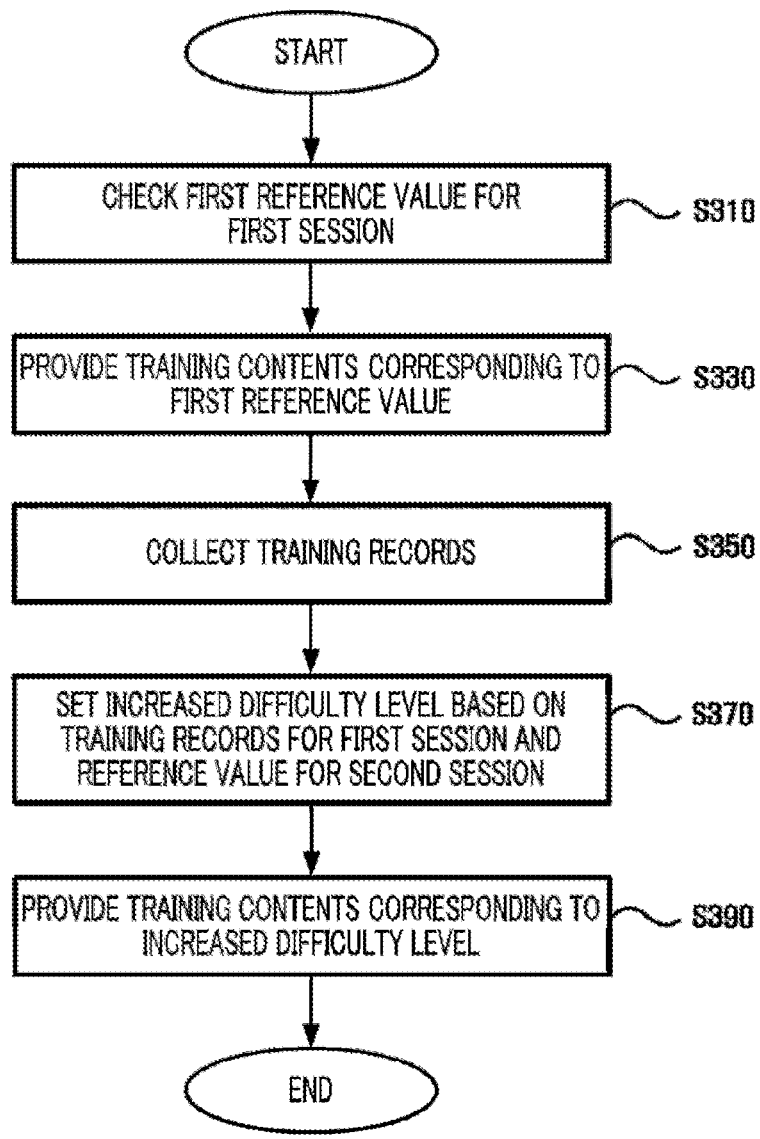

FIG. 4A
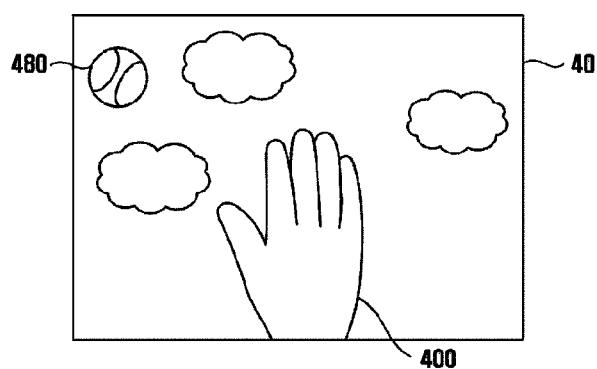
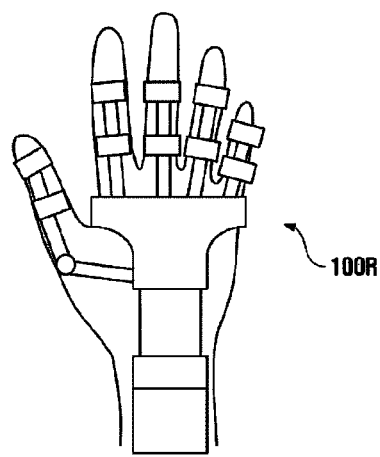

FIG. 4B
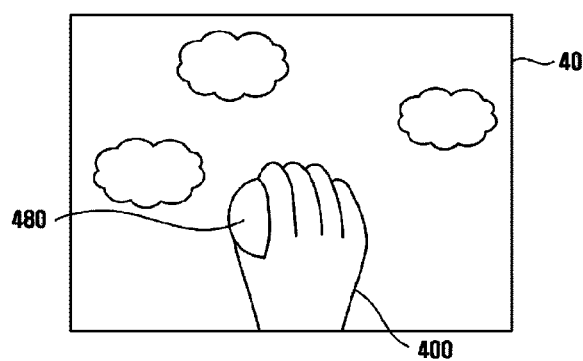
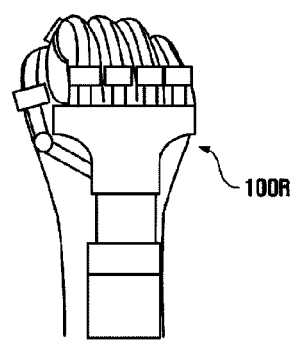

FIG. 5

| | |
|---|---|
| #1~#3 | 'MAXIMUM VALUE' * 'TRAINING TIME' * 0.3 |
| #4~#6 | 'MAXIMUM VALUE' * 'TRAINING TIME' * 0.4 |
| #7~#9 | 'MAXIMUM VALUE' * 'TRAINING TIME' * 0.5 |
| #10~#18 | 'MAXIMUM VALUE' * 'TRAINING TIME' * (0.5+ (int ( (session_num-1) / 3 ) - 2 ) /34) |
| #19~ | 'MAXIMUM VALUE' * 'TRAINING TIME' * (0.85-exp ( - (session_num/60 + 1.1) ) ) | ial
METHOD FOR SETTING DIFFICULTY LEVEL OF TRAINING CONTENTS AND ELECTRONIC DEVICE IMPLEMENTING THE SAME

CROSS-REFERENCE TO RELATED APPLICATION

This Application is the National Stage filing under 35 U.S.C. § 371 of PCT Application Ser. No. PCT/KR2017/008866 filed on Aug. 16, 2017, which claims the benefit of Korean Patent Application No. 10-2016-0107987 filed on Aug. 24, 2016. The disclosures of both applications are hereby incorporated herein by reference in their entireties.

TECHNICAL FIELD

Various embodiments of the present disclosure relate to a method for setting a difficulty level of training contents and an electronic device implementing the same, and more particularly to a method for setting a difficulty level of contents used for exercise or rehabilitation.

BACKGROUND

In the medical field, damage to the nervous system causes motor dysfunction and sensory dysfunction and also causes muscular atrophy, muscular stiffness, avacular necrosis, and the like. However, as for nervous diseases, treatments for removing only the causes thereof only are being mainly used, but there are not many treatments for restoring paralyzed motor function or sensory function caused by damage to the nerves.

The loss of motor function and sensory function inhibits the most basic activities for daily life, and the inability to use muscles for a long time causes muscular atrophy and muscular stiffness and the circulatory disturbance causes skin necrosis.

Recently, various rehabilitation devices have been introduced to rehabilitate motor function and sensory function. For example, there has been introduced a method by which electrical stimulation adjusted according to game information is applied to an area in need of rehabilitation when a patient plays a game containing using a game device.

However, such a rehabilitation device using game contents has been limited in that it has provided monotonous or typical game contents or programs. That is, conventional rehabilitation training contents using game contents have not considered the assumption that a user (e.g., patient) gets used to a rehabilitation device as he/she goes along, and, thus, when the user gets used to the corresponding training contents, it is difficult for him/her to receive rehabilitation training effectively.

DISCLOSURE OF THE INVENTION

Problems to be Solved by the Invention

The problem to be solved by the present disclosure is to provide a method for setting a difficulty level of training contents to be provided based on training of a user.

However, problems to be solved by the present disclosure are not limited to the above-described problems. Although not described herein, other problems to be solved by the present disclosure can be clearly understood by a person with ordinary skill in the art from the following description.

Means for Solving the Problems

To solve the above-described problem, a method for setting a difficulty level of training according to an aspect of the present disclosure is a method for setting a difficulty level of training of a user in a computing system that provides training contents, and includes: checking a first reference value, which is a preset difficulty level for a first session, if the user wants to perform a training motion of the first session; providing the user with training contents corresponding to the checked first reference value during the first session; collecting the user's training details of the training performed during the first session; setting an increased difficulty level based on a second reference value, which is a preset difficulty level for a second session and the user's training details collected during the first session, if the user wants to perform a motion of the second session; and providing the user with training contents corresponding to the set increased difficulty level during the second session.

In some embodiments, the first reference value, the second reference value, and the increased difficulty level may include at least one of motion time of the user or the number of times of motion for training contents to be performed by the user during the first session or the second session.

In some embodiments, the setting of the increased difficulty level may include setting, as the increased difficulty level, a value for internally dividing the second reference value and the user's training details of the training performed during the first session in a predetermined ratio.

In some embodiments, the method for setting a difficulty level of training may further include: collecting the user's training details of the training performed during the second session; calculating an average value of the user's training details collected during the first session and the user's training details collected during the second session; and checking a third reference value, which is a preset difficulty level for a third session, if the user wants to perform a motion of the third session and setting, as a new increased difficulty level, a value for internally dividing the average value and the third reference value in a predetermined ratio.

In some embodiments, the method for setting a difficulty level of training may further include: providing the user with training contents corresponding to the new increased difficulty level.

In some embodiments, the training contents may be contents that visually guide a rehabilitation motion of a patient.

An electronic device according to various embodiments of the present disclosure is an electronic device that provides training contents to a user and includes: a display unit; an information checking unit configured to check a first reference value, which is a preset difficulty level for a first session, if the user wants to perform a training motion of the first session; a contents providing unit configured to display, through the display unit, training contents corresponding to the checked first reference value; an information collecting unit configured to collect the user's training details of the training performed during the first session; and a training difficulty level setting unit configured to set an increased difficulty level based on a second reference value, which is a preset difficulty level for a second session and the user's training details collected during the first session, if the user wants to perform a motion of the second session, and the contents providing unit may display, through the display unit, training contents corresponding to the increased difficulty level during the second session.

In some embodiments, the training difficulty level setting unit may set, as the increased difficulty level, a value for internally dividing the first reference value and the user's training details in a predetermined ratio.

In some embodiments, the information collecting unit may collect the user's training details of the training performed during the second session, and the training difficulty level setting unit may calculate an average value of the user's training details collected during the first session and the user's training details collected during the second session and set, as a new increased difficulty level, a value for internally dividing the average value and a third reference value, which is a preset difficulty level for a third session, in a predetermined ratio.

In some embodiments, the training contents may be training contents that visually guide a rehabilitation motion of a patient, and the training difficulty level setting unit may display, through the display unit, training contents corresponding to the new increased difficulty level.

Other specific details of the present disclosure will be included in the detailed description and the accompanying drawings.

Effects of the Invention

According to the method for setting a difficulty level of training in various embodiments of the present disclosure, a difficulty level of training to be performed in the following session is set by considering a preset reference difficulty level and training details of based on training learning of the user, and, thus, it is possible to provide customized training contents more suitable for the user.

Further, effects to be achieved by the present disclosure are not limited to the above-described effects. Although not described herein, other effects to be achieved by the present disclosure can be clearly understood by a person with ordinary skill in the art from the following description.

BRIEF DESCRIPTION OF THE DRAWINGS

FIG. 3 is a flowchart showing an operation of setting a training difficulty level for a user by a computer system according to various embodiments of the present disclosure.

FIG. 4A and FIG. 4B are example diagrams illustrating that a user performs rehabilitation motions using training contents and a user-wearable device according to various embodiments of the present disclosure.

FIG. 5 and FIG. 6 are example diagrams showing preset reference values for respective sessions according to various embodiments of the present disclosure.

BEST MODE FOR CARRYING OUT THE INVENTION

Figure 1:
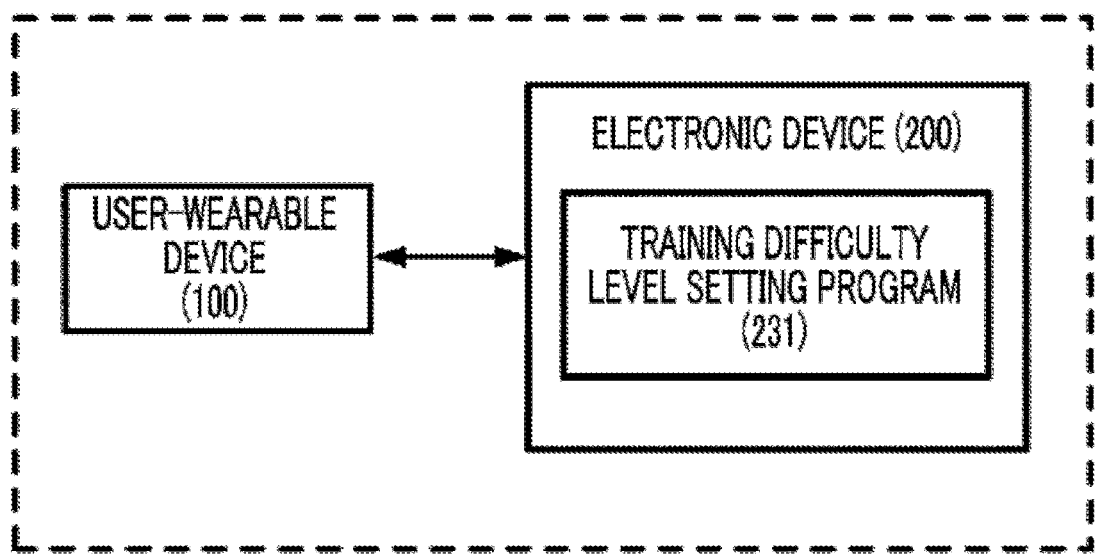
FIG. 1 is a block diagram illustrating a configuration of a training contents providing system according to various embodiments of the present disclosure.

The advantages and characteristics of the present disclosure and a method of achieving the advantages and characteristics will be clear by referring to exemplary embodiments described below in detail together with the accompanying drawings. However, the present disclosure is not limited to exemplary embodiment disclosed herein but will be implemented in various forms. The exemplary embodiments are provided by way of example only so that a person with ordinary skill in the art can fully understand the disclosures of the present disclosure and the scope of the present disclosure. Therefore, the present disclosure will be defined only by the scope of the appended claims.

The terms used herein provided only for illustration of the exemplary embodiments but not intended to limit the present disclosure. As used herein, the singular terms include the plural reference unless the context clearly indicates otherwise. The terms "comprises" and/or "comprising" specify the presence of stated components, but do not preclude the presence or addition of one or more other components. Throughout the whole specification, the same reference numerals denote the same elements, and the term "and/or" includes any and all combinations of one or more of the associated listed items. Although the terms "first", "second", and the like are used for describing various components, these components are not confined by these terms. These terms are merely used for distinguishing one component from the other components. Therefore, a first component to be mentioned below may be a second component in a technical concept of the present disclosure.

Unless otherwise defined, all terms (including technical and scientific terms) used herein have the same meaning as commonly understood by a person with ordinary skill in the art to which this invention pertains. It will be further understood that terms, such as those defined in commonly used dictionaries, should not be interpreted in an idealized or overly formal sense unless expressly so defined herein.

The term "training contents" used herein may refer to multimedia contents in which a motion of at least part of a user's body and an image object responding to the motion are displayed in real time through a display screen. The training contents may include various images, icons, or texts that guide the user to move for the purpose of exercise or rehabilitation.

The term "session" used herein may refer to the number of rounds the user receives training contents or the time training contents is provided for a corresponding round.

Hereafter, embodiments of the present disclosure will be described in detail with reference to the accompanying drawings.

FIG. 1 is a block diagram illustrating a configuration of a training contents providing system 10 according to various embodiments of the present disclosure.

As illustrated in the drawing, a training contents providing system may include a user-wearable device 100 and an electronic device 200. The training contents providing system 10 may be a home rehabilitation training system that visually guides a training of a user for the purpose of health or rehabilitation and may provide training contents to the user by various means such as augmented reality or virtual reality, but may not be limited thereto.

The user-wearable device 100 is an electronic device wearable on at least part of the user's body (e.g., hand, foot, or the like) to sense the user's motion. According to various embodiments, the user-wearable device 100 can be implemented as a wearable device. For example, the user-wearable device 100 may be an electronic device wearable on a hand as shown in FIG. 4A and FIG. 4B.

According to some embodiments, the user-wearable device 100 may include a control unit (e.g., processor, MCU, or the like), a communication unit (e.g., near field communication module or wireless communication module), a sensor unit, and a storage unit (e.g., memory).

As a non-limiting example, the sensor unit may include a 3-axis accelerometer, a 3-axis gyroscope, a 3-axis geomagnetic sensor, a bend sensor configured to measure a bending angle of a finger or a toe using various factors (e.g., resistance value), and the like.

In the embodiments of the present disclosure, the user-wearable device 100 is interlinked with the electronic device 200 to output the user's motions in real time through a display unit of the electronic device 200 based on signals generated according to the user's motions. Further, the user-wearable device 100 may record the the user's training details by digitizing the user's training details of the training performed for respective sessions and transfer the recorded user's training details to the electronic device 200 or an external server (not illustrated) through the communication unit.

The electronic device 200 is configured to provide training contents to the user based on the user's training details received from the user-wearable device 100 and a preset training difficulty level. The electronic device 200 may include a training difficulty level setting program 231 and perform a function by executing the training difficulty level setting program 231 under the control of the control unit. A detailed configuration of the electronic device 200 will be described later.

Although not illustrated in FIG. 1, the training contents providing system 10 may further include an external server. The external server may communicate with the user-wearable device 100 or the electronic device 200 to receive the user's training details or set training contents to be provided to the user or a difficulty level of the training contents. According to various embodiments, the external server may be implemented to include a control unit or functional components (e.g., information checking unit, training difficulty level setting unit, information collecting unit, and program providing unit) of the control unit which will be described later with reference to FIG. 2.

Figure 2:
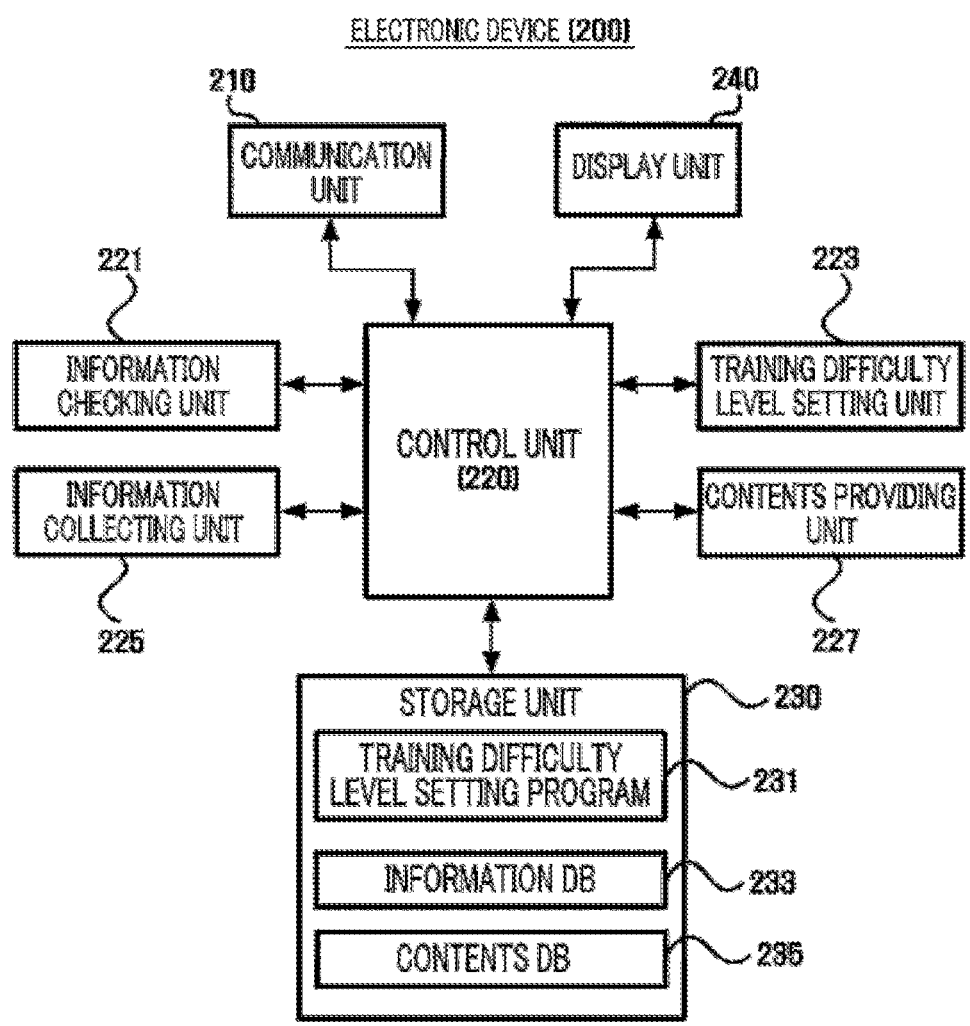
FIG. 2 is a block diagram illustrating an electronic device that provides training contents according to various embodiments of the present disclosure.

FIG. 2 is a block diagram illustrating the electronic device 200 that provides training contents according to various embodiments of the present disclosure.

As shown in the drawing, the electronic device 200 may include a communication unit 210, a control unit 220, an information checking unit 221, a training difficulty level setting unit 223, an information collecting unit 225, a contents providing unit 227, a storage unit 230, and a display unit 240. As a non-limiting embodiment, the electronic device 200 may not include at least some of the components illustrated in FIG. 2 or may further include additional components.

The communication unit 210 may connect communication between the user-wearable device 100 and the electronic device 200. For example, the communication unit 210 can establish communication connection with the user-wearable device 100 through a near field communication module (e.g., RF module, WIFI module, GPS module, Bluetooth module, Zigbee module, NFC module, or the like) or a wired communication module (e.g., terminal, or the like). The communication unit 210 can also be connected to the external server via a network (not illustrated).

The control unit 220 may perform general operations such as controlling the supply of power to the electronic device 200 and a data processing function of controlling the flow of signals among internal components of the electronic device 200 and processing data. The control unit 220 may include at least one processor, and the processor may include one or more of a central processing unit (CPU), an application processor (AP), or a communication processor (CP).

The information checking unit 221 may check preset difficulty levels for respective training sessions which the user train, information collected from the user-wearable device 100, or information stored in the storage unit 230 of the electronic device 200 and transfer the checked information to the control unit 220, the training difficulty level setting unit 223, the information collecting unit 225, and the contents providing unit 227.

The training difficulty level setting unit 223 may set a difficulty level of training contents based on the preset difficulty levels (e.g., reference values) for the respective sessions and the user's training details collected from the user-wearable device 100.

The information collecting unit 225 may collect, from the user-wearable device 100, the user's training details of the training performed during the respective sessions and transfer the collected information to at least some components of the electronic device 200.

The contentd providing unit 227 may check the difficulty level of training contents which has been set by the training difficulty level setting unit 223, retrieve the training contents stored in the storage unit 230, and prepare the training contents according to the difficulty level. Then, the contents providing unit 227 may display the prepared training contents through the display unit 240 in response to the user's request.

According to various embodiments, the contents providing unit 227 may project at least part of the user's body (e.g., hand, foot, or the like) on the display unit 240 based on the information collected form the user-wearable device 100. For example, the contents providing unit 227 may project and display the user's hand on the display unit 240, and in this case, an object to be moved according to a motion of the user's hand in a virtual space may be displayed through the display unit 240.

The storage unit 230 may store data received or generated from the control unit 220 and the electronic device 200 or other components of the training contents providing system 10. The storage unit 230 may include, for example, a memory, a cache, a buffer, or the like and may be composed of software, firmware, hardware, or a combination of at least two thereof.

According to various embodiments, the storage unit 230 may include the training difficulty level setting program 231. The training difficulty level setting program 231 may be executed by a computing system (e.g., the electronic device 200 등) to set or change a difficulty level of training contents provided by the computing system. The training difficulty level setting program 231 may be implemented as an application which can be downloaded from the external server or as being embedded in the electronic device 200, but may not be limited thereto.

According to various embodiments, the storage unit 230 may include an information DB 233 and a contents DB 235. The information DB 233 and the contents DB 235 are illustrated as being separate from each other in the storage unit 230, but may not be limited thereto and may be configured as a single module.

The information DB 233 may store various data generated when the function of the training difficulty level setting program 231 is executed and data collected from the user-wearable device 100. Further, the information DB 233 may store preset data. The preset data may include, for example, reference values which are difficulty levels of training contents to be provided for respective sessions, user information (e.g., name, age, height, weight, kind of disease, medical care information), and the like, but may not be limited thereto.

The contents DB 235 may store training contents to be output on the display unit 240 when the function of the training difficulty level setting program 231 is executed. The training contents may be added, changed, or deleted in real time, regularly, or at random points in time.

The above-described the information checking unit 221, the training difficulty level setting unit 223, the information collecting unit 225, and the contents providing unit 227 may be components logically or functionally divided according to the respective functions of the control unit 220. Therefore, the information checking unit 221, the training difficulty level setting unit 223, the information collecting unit 225, and the contents providing unit 227 may also be configured as a single unit together with the control unit 220.

Further, the functions of the information checking unit 221, the training difficulty level setting unit 223, the information collecting unit 225, the contents providing unit 227, and the control unit 220 may be implemented in the form of a routine, instructions, or a program (e.g., training difficulty level setting program 231) stored in the storage unit 230 (e.g., memory).

Furthermore, the routine, the instructions, or the program may be stored in a computer-readable storage medium. Such a storage medium may include all types of storage media which store a program and data readable by a computer system. For example, the storage medium may include a read only memory (ROM), a random access memory (RAM), a compact disc (CD), a digital video disc (DVD)-ROM, a magnetic tape, a floppy disc, an optical data storage device, a flash memory, or the like. In addition, such a storage medium may be distributed to a computer system connected to a network, and a computer-readable code may be stored and executed on a distributed basis in the storage medium.

The display unit 240 may display the training contents or the information collected from the user-wearable device 100. The display unit 240 may include, for example, a liquid crystal display (LCD), a light-emitting diode (LED) display, an organic light-emitting diode (OLED) display, or a microelectromechanical systems (MEMS) display, or an electronic paper display. For example, the display 240 may display various types of contents (e.g., texts, images, videos, icons, or symbols) to the user. Further, the display 240 may include a touchscreen and may receive a touch, gesture, proximity, or hovering input by using, for example, an electronic pen or a portion of the user's body.

FIG. 3 is a flowchart showing an operation of setting a training difficulty level for a user by a computer system (e.g., electronic device 200) according to various embodiments of the present disclosure.

To explain each of the processes shown in FIG. 3, the user-wearable device 100 and the training difficulty level setting program 231 may be preset or operated. For example, the user may turn on the user-wearable device 100 and the electronic device 200 and wear the user-wearable device 100.

According to various embodiments, the electronic device 200 may execute the training difficulty level setting program 231 to perform customizing to the user wearing the user-wearable device 100. The customizing is to guide, through the display unit 240, the user to perform a motion such as moving, bending, or twisting at least part of his/her body (e.g., fingers or wrist) as much as possible while the user wears the user-wearable device 100. Thus, the electronic device 200 can collect threshold values for respective user states and set a difficulty level of the training contents in further consideration of the collected threshold values.

Figure 6:
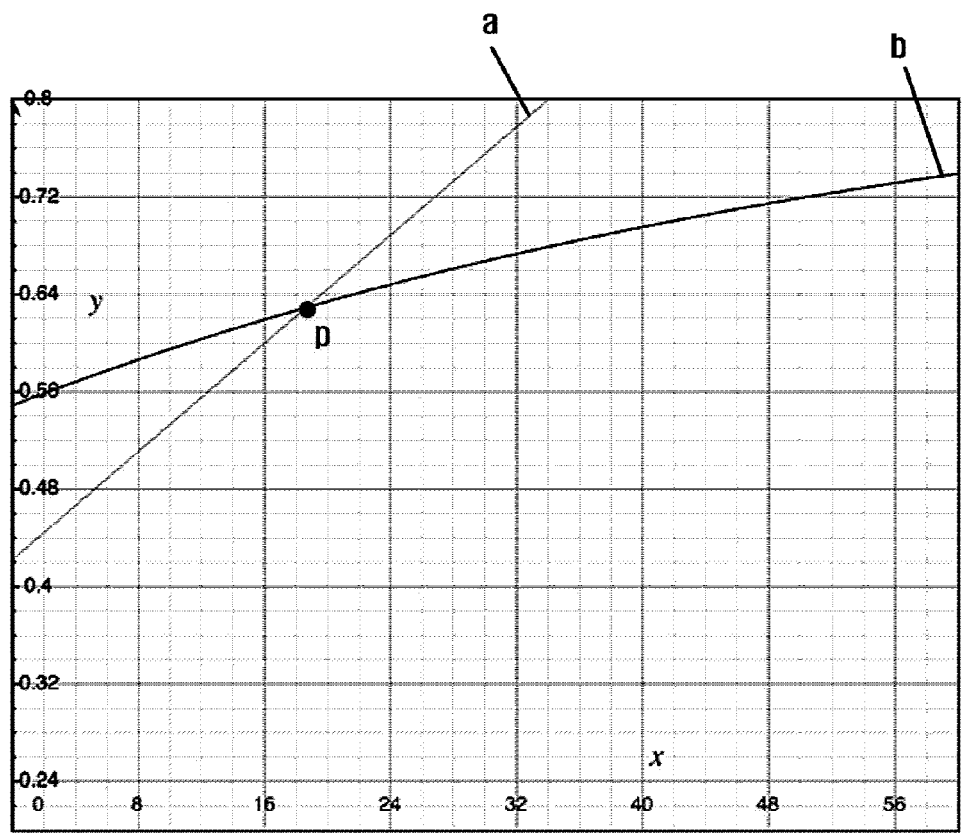

Further, as a non-limiting assumption, the training contents described with reference to FIG. 3 are assumed as contenta that visually guide a rehabilitation motions of a patient. Furthermore, the flowchart shown in FIG. 3 will be explained with reference to FIG. 5 and FIG. 6. FIG. 5 and FIG. 6 are example growth curves for calculating preset reference values for respective sessions according to various embodiments of the present disclosure.

As shown in FIG. 3, when the user wants to perform a training motion of a first session, the electronic device 200 or the training difficulty level setting program 231 may check a first reference value for the first session (S310). The first reference value is a preset difficulty level for the first session, and the preset difficulty level may include at least one of the number of times of motion or motion time for training contents to be achieved by the user. The first session and a second session and a third session to be described later are examples suggested to explain sessions corresponding to before and after a certain point in time, but the embodiments of the present disclosure may not be limited thereto.

FIG. 5 and FIG. 6 show a growth curve equation by which reference values can be determined. FIG. 5 shows difficulty levels calculated for respective sessions, and FIG. 6 shows a growth curve equation which is graphed on the basis of FIG. 5. The difficulty levels calculated in FIG. 5 may be calculated on the basis of the user's past records or average past records of other users, but may not be limited thereto.

For example, according to predetermined policies (e.g., equation) as shown in FIG. 5, the reference values may be set on the basis of a maximum value (e.g., difficulty level calculated on the basis of end users), training time, a specific coefficient, and a session number. The curve for the reference values shown in FIG. 5 is as shown in FIG. 6. As a non-limiting example, the growth curve equation may be set on the basis of minimum values on overlapping graphs for each session. For example, from a session number 0 to a point P, a difficulty level (y value) on a graph a may be a growth curve equation (i.e., reference value) for the corresponding session and from the point P, a difficulty level on a graph b may be a growth curve equation for the corresponding session.

Then, the electronic device 200 or the training difficulty level setting program 231 may provide the user with training contents corresponding to the first reference value (S330). For example, the electronic device 200 may adjust the number of times of training or training time of the user in the training contents according to the difficulty level corresponding to the first reference value and display or play the adjusted training contents through the display unit 240 during the first session.

Then, the electronic device 200 or the training difficulty level setting program 231 may collect the user's training details of the training performed during the first session (S350). To this end, the electronic device 200 may generate training records which are digitized from the training details based on signals collected from the user-wearable device 100. For example, the training records may refer to the number of times of motion or motion time achieved by the user during previous sessions. The training records may be generated by the electronic device 200 or may also be generated by the user-wearable device 100.

Then, the electronic device 200 or the training difficulty level setting program 231 may determine an increased difficulty level based on the training records for the first session and a reference value for a second session subsequent to the first session (S370). The increased difficulty level may be a difficulty level which is set on the basis of, for example, the preset reference value and the user's training records of the training performed during the previous sessions.

According to various embodiments, the electronic device 200 or the training difficulty level setting program 231 may set a value for internally dividing the first reference value and the user's training records of the training performed in the first session in a predetermined ratio. For example, the electronic device 200 or the training difficulty level setting program 231 may calculate an increased difficulty level for internally dividing the training records recorded in the first session and a reference value for the second session in 2:1 according to the following equation. The following mathematical equation is illustrative, but the embodiments of the present disclosure are not limited thereto.

$$G_2 = \frac{T_2}{3} \times \left(\frac{C_2}{T_2} + 2\frac{S_1}{T_1}\right) \times \frac{A_1}{A_2} \times (1 + \text{Random}() \times 0.1) \quad \text{[Equation 1]}$$

Herein, reference values for a previous session and the present session (e.g., constant or variable) are C 1 and C 2, respectively; the target numbers of successes for the previous session and the present session are G 1 and G 2, respectively; the actual number of successes for the previous session is S1; AROM for the previous session and the present session is A 1 and A 2, respectively; training times for the previous session and the present session are T 1 and T 2, respectively; and retention times for the previous session and the present session are M 1 and M 2, respectively. Herein, the AROM refers to a value for active range of motion. As such, the training difficulty level setting program 231 may calculate an increased difficulty level in consideration of the training records in the previous session (e.g., number of successes, training time, retention time, and the like) and the reference value which is a preset difficulty level for the present session (e.g., equation reference value, target number of successes, AROM value, training time, retention time).

As another embodiment for calculating an increased difficulty level, the electronic device 200 or the training difficulty level setting program 231 may calculate an average value of the training records of N number of previous sessions and set, as a new increased difficulty level, a value for internally dividing the average value and a reference value for a new session (e.g., third session) in a predetermined ratio.

As a non-limiting embodiment, the electronic device 200 or the training difficulty level setting program 231 may calculate a new increased difficulty level according to the following mathematical equation.

$$G_n = \frac{T_2}{3} \times \left( \frac{C_2}{T_2} + 2 \left( \frac{\sum_{i=1}^{n}(n+1-i) \times \frac{S_i^p}{T_i^p}}{\frac{1}{2}n(n+1)} \right) \right) \times \quad \text{[Equation 2]}$$

$$\frac{A_1}{A_2} \times (1 + \text{Random}() \times 0.1)$$

Herein, S p i refers to an ith previous record and T p i refers to an ith previous attempted training time.

For example, the electronic device 200 or the training difficulty level setting program 231 may calculate an average value of the user's training details collected during the first session and the user's training details collected during the second session. Then, if the user wants to perform a motion of the third session, the electronic device 200 or the training difficulty level setting program 231 may check a third reference value which is a preset difficulty level for the third session and calculate a new increased difficulty level for internally dividing the average value and the third reference value in a predetermined ratio (e.g., 2:1).

Further, according to some embodiments, the electronic device 200 or the training difficulty level setting program 231 may select a predetermined number of (e.g., N number of) training records recently received from previous sessions and calculate an average value thereof. In this case, the electronic device 200 or the training difficulty level setting program 231 may calculate the average value by giving a higher weight to a more recent record among the N number of training records. Thus, the electronic device 200 or the training difficulty level setting program 231 may set a more accurate difficulty level of training in further consideration of recent state information of the user (e.g., patient).

The above method for setting an increased difficulty level has been described with reference to the example equation, but various embodiments of the present disclosure may not be limited thereto.

Referring to FIG. 2, the electronic device 200 or the training difficulty level setting program 231 may provide the user with training contents corresponding to the calculated increased difficulty level (S390). For example, the electronic device 200 or the training difficulty level setting program 231 may check new training contents corresponding to the calculated increased difficulty level, or may set the difficulty level of the existing training contents to the calculated increased difficulty level and then provide the training contents to the user. The training contents may be provided to the user by, for example, outputting the training contents through the display unit 240 of the electronic device 200.

FIG. 3 illustrates that the processes are performed in sequence, but the present disclosure is not limited thereto. For example, the order of the processes illustrated in FIG. 3 may be changed, and at least some processes may be omitted or added.

According to the above-described embodiment, if the user of the present disclosure is a patient who wants to get rehabilitation treatment, he/she can get the rehabilitation treatment at home with ease and fun without the help of a therapist or a doctor. In this case, a difficulty level is automatically adjusted depending on the use by the patient, and, thus, effects of the treatment can be maximized.

Further, if the user of the present disclosure is a user who wants to take exercise for the purpose of improving his/her fitness, he/she can take exercise at home with ease and fun without the help of a personal trainer or the like.

FIG. 4A and FIG. 4B are example diagrams illustrating that a user performs rehabilitation motions using training contents and the user-wearable device 100 according to various embodiments of the present disclosure.

FIG. 4A and FIG. 4B are diagrams illustrating an example of a motion of a user-wearable device 100R for right hand rehabilitation and an example of a game screen displayed through the electronic device 200.

The electronic device 200 may store various kinds of exercise games relating to at least part of the body as various embodiments of training contents. For example, the electronic device 200 may store a game for rehabilitation exercise for wrist, a game for rehabilitation exercise for fingers, and the like. Each game may be implemented to repeat a specific hand motion. For example, each game may be implemented to repeat one of a motion of pouring water into a cup, a motion of catching a moving fish, a motion of catching a flying butterfly, a motion of fanning oneself, a motion of opening a bottle, a motion of catching a throwing ball, a motion of turning over leaves of a book, a motion of painting a fence with a brush, and a motion of pouring wine, but these motions are illustrative and the embodiments of the present disclosure are not limited thereto.

If a list of the above-described games is displayed through the display unit 240 of the electronic device 200, the user may select a required or desired game. If a game is selected, the control unit 220 of the electronic device 200 may configure a game screen for the selected game. For example, if a game for repeating a motion of catching a ball is selected, the display unit 240 of the electronic device 200 may display the game screen 40 as shown in FIG. 4A.

Referring to FIG. 4A, a ball-shaped graphic object 480 and a right hand-shaped graphic object 400 are placed in the game screen 40. The right hand-shaped graphic object 400 moves in response to a motion of the user-wearable device 100R for right hand rehabilitation. As shown in FIG. 4A, if all of the fingers of the user-wearable device 100R for right hand rehabilitation are stretched, the right hand-shaped graphic object 400 displays stretched fingers.

When a game is played, the ball-shaped graphic object 480 moves gradually towards the right hand-shaped graphic object 400. Upon checking a motion of the ball-shaped graphic object 480, the user makes a gesture of catching a ball. For example, as shown in FIG. 4B, if the user makes a gesture of bending all his/her fingers, multiple finger sensing units of the user-wearable device 100R for right hand rehabilitation that are assigned to the respective fingers bend as well. As a result, the right hand-shaped graphic object 400 displays bent fingers.

If the user succeeds or fails in catching the ball-shaped graphic object 480, a success or failure message may be output through an output unit (not illustrated) of the electronic device 200. The notification message may be printed out as a visual signal, an audio signal, a tactile signal, an optical signal, or a combination thereof. Apart from the success in the game, additional information like the goal that the user has to achieve, the number of successes, and the number of times of motion may be displayed in a specific area on the game screen.

In addition to FIG. 4A and FIG. 4B illustrating the example of the training contents, the goal for the training contents (e.g., game), the number of successes, and the number of times of motion, or motion time to be achieved may be set as a difficulty level of the training contents according to the embodiment of the present disclosure. Further, an increased difficulty level may be set on the basis of details of the training performed by the user during respective session where the user receives training contents and preset reference values for the respective sessions, and training contents corresponding to the increased difficulty level may be provided differently for each of the sessions.

FIG. 4A and FIG. 4B illustrate the game screen 40 in two dimensions but the kinds of game images are not limited thereto. According to another embodiment, game images can be three-dimensional images of a virtual three-dimensional space as seen from a specific view. In this case, the ball-shaped graphic object 480 and the right hand-shaped graphic object 400 can be expressed as a three-dimensional graphic object and placed in the virtual three-dimensional space. According to another embodiment, the game image can be an AR (Augmented Reality) image matching the ball-shaped graphic object 480 or the right hand-shaped graphic object 400 on an actual image obtained by taking a real-world environment.

Although FIG. 4A and FIG. 4B illustrate the case where the game screen 40 is displayed through the electronic device 200, the training contents provided through the electronic device 200 is not limited to the game screen 40.

The processes of a method or algorithm described in connection with the embodiments disclosed herein may be embodied directly in hardware, in a software module executed by hardware, or in a combination of the two. The software module may reside in RAM (Random Access Memory), ROM (Read Only Memory), EPROM (Erasable Programmable ROM), EEPROM (Electrically Erasable Programmable ROM), flash memory, hard disc, a removable disc, a CD-ROM, or any other form of computer-readable storage medium known in the art.

Although the exemplary embodiments of the present disclosure have been described with reference to the accompanying drawings, it would be understood by a person with ordinary skill in the art that various changes and modifications may be made without changing technical conception and essential features of the present disclosure. Thus, it should be understood that the above-described embodiments are illustrative in all aspects and do not limit the present disclosure.

We claim:

1. A method for setting a difficulty level of training of a user in a computing system that provides training contents, the method comprising:

checking a first reference value, which is a preset difficulty level for a first session, if the user wants to perform a training motion of the first session;

providing the user with training contents corresponding to the checked first reference value during the first session;

collecting the user's training details of the training performed during the first session;

setting an increased difficulty level based on a second reference value, which is a preset difficulty level for a second session, and the user's training details collected during the first session, if the user wants to perform a training motion of the second session; and providing the user with training contents corresponding to the set increased difficulty level during the second session, wherein the collecting of the user's training details of the training includes collecting the user's training details of the training performed in sessions before an Nth session; and wherein the setting of the increased difficulty level includes:

calculating an average value of a predetermined number of training records among the user's training details collected during the sessions before the Nth session by giving a greater weight to more recent training records; and checking a reference value, which is a preset difficulty level for the Nth session and setting, as a new increased difficulty level, a value for internally dividing the average value and the reference value in a predetermined ratio.

2. The method for setting a difficulty level of training of claim 1, wherein the first reference value, the second reference value, and the increased difficulty level include at least one of motion time of the user or the number of times of motion for training contents to be performed by the user during the first session or the second session.

3. The method for setting a difficulty level of training of claim 1, further comprising:
providing the user with training contents corresponding to the new increased difficulty level.

4. The method for setting a difficulty level of training of claim 3, wherein the training contents are contents that visually guide a rehabilitation motion of a patient.

5. An electronic device that provides training contents to a user, the electronic device comprising:
a display unit;
an information checking unit configured to check a first reference value, which is a preset difficulty level for a first session, if the user wants to perform a training motion of the first session;
a contents providing unit configured to display, through the display unit, training contents corresponding to the checked first reference value;
an information collecting unit configured to collect the user's training details of the training performed during the first session; and
a training difficulty level setting unit configured to set an increased difficulty level based on a second reference value, which is a preset difficulty level for a second session and the user's training details collected during the first session, if the user wants to perform a motion of the second session,
wherein the contents providing unit displays, through the display unit, training contents corresponding to the increased difficulty level during the second session,
the information collecting unit is further configured to collect the user's training details of the training performed in sessions before an Nth session; and
the training difficulty level setting unit is further configured to calculate an average value of a predetermined number of training records among the user's training details collected during the sessions before the Nth session by giving a greater weight to more recent training records, check a reference value, which is a preset difficulty level for the Nth session and set, as a new increased difficulty level, a value for internally dividing the average value and the reference value in a predetermined ratio.

6. The electronic device of claim 5,
wherein the training contents are training contents that visually guide a rehabilitation motion of a patient, and
the training difficulty level setting unit displays, through the display unit, training contents corresponding to the new increased difficulty level.

* * * * *